United States Patent [19]

Pashley

[11] Patent Number: 4,538,990

[45] Date of Patent: Sep. 3, 1985

[54] METHOD OF DECREASING THE PERMEABILITY OF A DENTAL CAVITY

[75] Inventor: David H. Pashley, Augusta, Ga.

[73] Assignee: Medical College of Ga. Research Institute, Inc., Augusta, Ga.

[21] Appl. No.: 653,321

[22] Filed: Sep. 24, 1984

[51] Int. Cl.$^3$ ............................................. A61K 6/08
[52] U.S. Cl. ..................................... 433/217; 106/35
[58] Field of Search ................ 523/116, 118; 106/35; 433/217

[56] References Cited

U.S. PATENT DOCUMENTS 3,471,927  10/1969  Eisenberg ............................ 106/35
4,396,378  8/1983  Orlowski et al. ..................... 106/35
4,496,322  1/1985  Sandham et al. ..................... 106/35

*Primary Examiner*—Lorenzo B. Hayes
*Attorney, Agent, or Firm*—William H. Needle

[57] ABSTRACT

A method of decreasing the permeability of dental cavity preparations comprising the steps of first applying from 1 to 30% w/v neutral oxalate salt solution, such as dipotassium oxalate to the smear layer and then applying 0.5 to 3% w/v of an acidic oxalate salt solution, such as a monopotassium monohydrogen oxalate, to the layer. The resultant layer of microscopic calcium oxalate crystals makes the dentin surface more resistant to acid attack.

9 Claims, No Drawings

METHOD OF DECREASING THE PERMEABILITY OF A DENTAL CAVITY

BACKGROUND OF THE INVENTION

When dentists are finished preparing a cavity in a tooth to receive a restorative material, they almost always line the cavity with a material called a "cavity liner" or "cavity varnish." That material is supposed to decrease the permeability of the dentin to any of the potentially injurious materials placed in the cavity during its restoration or to any microbial products from the oral fluids that might gain access to the inner parts of the cavity in the event that the restorative material might permit microleakage around its margins with the tooth. The most popular cavity varnishes contain organic "gums" dissolved in organic solvents. When the organic solvent evaporates, a thin film of this organic material remains on the dentin.

The disadvantages of the old cavity lining agents are that they are composed primarily of water-insoluble organic material which can only lay on top of a liquid layer that covers the surface of the dentin without any type of bond. This makes for a very leaky junction or union. The lack of adherence of the old cavity varnishes is such that they can wash out if the restoration leaks. If there is any gap or space between the restoration and the tooth, the lining varnish can move up or down depending on the direction of the forces of the leaking restoration.

The "smear layer" of microcrystalline debris, which is formed on the surface of all cut dentin, provides a natural cavity liner. It occludes the orifices of dentinal tubules to the point where bacteria cannot gain access to the tubules. Unfortunately, the particle size of the constituents making up the smear layer are so small that they have an enormous surface/volume ratio, making them extremely acid-labile. If there is any microleakage around the filling material and/or old-style cavity varnish, the smear layer is quickly dissolved.

The prior art includes U.S. Pat. No. 4,057,621 which discloses the use of oxalate salts to desensitize hypersensitive dentin or cementum sufaces teeth; and U.S. Pat. No. 2,746,905 which discloses the use of dehydroacetic acid and its water-soluble salts to maintain the pH of the mouth above 5.2 to prevent the dissolution of inorganic tooth enamel material and includes the use of oxalate in the composition as an enamel protective agent to increase the resistance of the tooth to acid attack.

SUMMARY OF THE INVENTION

The disadvantages of the prior art are overcome by the present invention which relates to a method of decreasing the permeability of a dental cavity prepared to receive restorative material and which also makes the dentin surface resistant to acid attack. The method involves the sequential application of two oxalate salts to the smear layer. First, from 1 to 30% w/v of a neutral oxalate salt solution such as dipotassium oxalate is applied and then followed within one to two minutes by an application of from 0.5 to 3% w/v of an acidic oxalate salt solution, such as monopotassium monohydrogen oxalate. The neutral oxalate forms large calcium oxalate crystals all over the dentin surface, while the acid oxalate forms smaller crystals around the previously precipitated larger crystals to form a uniform layer of microscopic crystals. These crystals actually form in the dentin surface and grow out of the surface, remaining firmly attached thereto.

The advantages of this type of cavity lining material over the prior art is that (1) it forms a crystalline lining layer on top of a crystalline smear layer, and (2) it transforms the smear layer from a highly acid-labile structure to one which is acid resistant.

DETAILED DESCRIPTION OF THE ILLUSTRATIVE EMBODIMENTS

When soluble oxalate salts are placed on dentin, they react with ionized calcium present in dentinal fluid to form a precipitate of calcium oxalate which is a very insoluble precipitate whose crystal sizes are smaller than the size of dentinal tubules. This permits the precipitate to fall down into the tubules where they can reduce dentin permeability in the event that the restorative material placed on it develops some microleakage.

The present invention first utilizes from 1–30% w/v of a neutral oxalate salt solution on the dentin. The preferred salt is dipotassium oxalate, but all of the alkalai metal salts, as well as the ammonium salts, of oxalate are effective. Additionally, other metal salts, such as the salts of aluminum, zinc, copper, nickel, colbalt, iron and manganese, are effective up to saturation of their solutions. However, many metal salts of oxalate are not as soluble as potassium oxalate and are, therefore, less effective.

The dentin surface is then treated with an acidic oxalate solution, preferably 0.5 to 3% w/v of monopotassium monohydrogen oxalate. The preferred concentration is 3%.

As the crystals resulting from dipotassium oxalate treatment are large (i.e., relative to dental tubules diameter) crystals of calcium oxalate dihydrate, the dipotassium oxalate should be applied first in as high a concentration as possible (for instance, a saturated 30% solution), to permit large crystals of insoluble calcium oxalate dihydtrate ($K_{sp}$ $2.57 \times 10^{-9}$) to form in dental tubules. The source of the calcium for this reaction is thought to be the ionized, soluble calcium in dentinal fluid wetting the smear layer debris. The reaction of the dipotassium oxalate with the calcium ions is as follows:

$$K_2C_2O_4 + Ca^{++} + 2H_2O \rightarrow CaC_2O_4.2H_2O \downarrow$$

The reaction can be driven to completion by applying as concentrated a solution of monopotassium-monohydrogen oxalate as possible (for instance 3% w/v), two to four minutes later. This second oxalate solution is acidic enough to solubilize local hydroxyapatite, raising the local ionized calcium and phosphate concentrations to the point where it completes the precipitation of oxalate as calcium oxalate in several forms. These smaller crystals tend to fill in any microscopic spaces around the larger oxalate crystals, increasing the effectiveness of these precipitates and reducing dentin permeability. Therefore, the order of application should be the neutral, 30% dipotassium oxalate, followed by the acid 3% monopotassium-monohydrogen oxalate. Lower concentrations of these oxalate salts are less effective.

The calcium oxalate crystals actually bind to the microcrystalline cutting debris which constitute the smear layer covering both enamel and dentin. In this sense, they create a protective layer of acid-resistant crystals on top of the smear layer of smear plugs in the dentinal tubules. They also cover the smear layer laying on top of cut enamel surfaces. At the molecular level, it is thought that the two ionized carboxyl groups of dipotassium oxalate bind both to surface calcium atoms and to calcium ions in solution, thereby promoting rapid crystal growth of calcium oxalate dihydrate which is firmly attached to smear layer particles. This reaction occurs rapidly within seconds to minutes, resulting in crystals forming within the fluid-filled interstitial spaces between smear layer particles, as well as covering all exposed surfaces of these particles, thereby protecting them from acid dissolution which would increase the sensitivity of the vital dentin.

When 3% monopotassium-monohydrogen oxalate (pH 2.0) reacts with dentin, it initiates a very complex set of reactions which probably include the following:

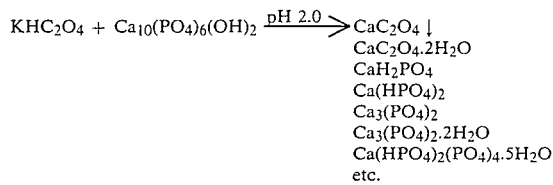

This form of oxalate produces its own ionized calcium by acid etching the hydroxyapatite of dentin, thereby providing enough calcium to precipitate all of the oxalate. Additionally, it leads to the precipitation of a host of other relatively insoluble calcium salts, most of which have very small crystal sizes and low acid solubilities. The solutions can be carried to the cavity by a saturated cotton ball or via a small dispenser.

The following tests, summarized in Table I, were conducted to demonstrate the ability of the oxalate salts to decrease dentin permeability and to transform the smear layer from an acid-labile to an acid resistant surface:

Briefly, dentin discs were prepared and their permeability determined as previously described (Pashley, Thompson and Stewart, J. Dent. Res. 62(9): 956–959, 1983). The permeability of dentin with a smear layer on its surface was 0.039 $\mu l\ cm^{-2}min^{-1}cmH_2O^{-1}$ (Table I). When dentin with a smear layer was acid etched for two minutes with 6% citric acid, the dentin permeability increased 439% to 0.173. If, on the other hand, the smear layer was treated with 30% dipotassium oxalate, dentin permeability fell to 26% of its original value (a 74% reduction) or a value of 0.017. When an oxalate-treated smear layer was then acid-etched for two minutes with 6% citric acid, dentin permeability only increased to a value of 0.018 (a 6% increase) rather than the expected 439% increase. Similarly, treating dentin with a smear layer with 3% monopotassium-monohydrogen oxalate caused the dentin permeability to fall from 0.039 to 0.002. Further, attempts to acid etch this oxalate-treated dentin with 6% citric acid produced no change in dentin permeability, rather than the expected 439% increase. Treating the smear layer with 30% dipotassium oxalate for two minutes, followed by 3% monopotassium-monohydrogen oxalate for another two minutes yielded essentially the same results, (i.e., a reduction in dentin permeability and the transformation of an acid-labile smear layer into an acid-resistant surface). Scanning electron microscopy (SEM) of these specimens suggests that the sequential use of both oxalate solutions may be more desirable as a cavity lining agent than either agent alone.

The tests show that the insoluble calcium oxalate crystals on the smear layer or dentin surface are not solubilized by a two-minute exposure of citric acid, an acid that is commonly used for that duration therapeutically in dentistry. The treated surface is not necessarily impermeable to acids; however, the treated smear layer remains in place and the permeability of dentin remains low but finite (not permeable) rather than showing a large increase (400–1,000%) in permeability that always accompanies acid exposure of non-treated smear layer dentin.

TABLE I

The effects of oxalate-treatment and acid etching on dentin permeability as measured by the hydraulic conductance (Lp) of dentin.

| | Lp (in $\mu l\ cm^{-2}min^{-1}cmH_2O^{-1}$)+ | | |
|---|---|---|---|
| Dentin treatment | Dentin w/smear layer | p values* | Acid-treated dentin |
| 3% KCl (control) | $3.94 \times 10^{-2} \pm 1.63 \times 10^{-2}(18)$ | <0.005 | $1.73 \times 10^{-1} \pm 3.35 \times 10^{-2}(18)$ |
| 30% K$_2$Oxalate | $1.71 \times 10^{-2} \pm 9.50 \times 10^{-3}(12)$ NS $p < 0.05$* | NS | $1.83 \times 10^{-2} \pm 1.52 \times 10^{-2}(6)$ $p < 0.005$ $p < 0.001$ |
| 3% KHOxalate | $2.10 \times 10^{-3} \pm 9.10 \times 10^{-4}(6)$ $p = 0.05$ | NS | $1.15 \times 10^{-3} \pm 5.30 \times 10^{-4}(6)$ $p < 0.001$ |
| 30% + 3% Oxalates | $4.86 \times 10^{-3} \pm 4.03 \times 10^{-3}(6)$ | NS | $5.40 \times 10^{-4} \pm 4.10 \times 10^{-4}(6)$ |

+Values expressed as the $\bar{x} \pm$ SEM of the Lp; number in parentheses indicates the number of specimens tested.
*Student's t test, two tailed, unpaired, comparing oxalate and acid-treated values with controls.
NS Not statistically significant.

What I claim is:

1. A method of decreasing the permeability of a prepared dental cavity surface, comprising the steps of:
    (a) treating said cavity surface prior to receiving a restorative material with an effective amount of a neutral oxalate salt solution to form an acid resistant first surface; and
    (b) applying to said first surface, at a predetermined amount of time after step (a) an effective amount of an acidic oxalate salt solution to form an acid resistant second surface, thereby forming an acid resistant liner on said dental cavity surface.

2. A method as claimed in claim 1 wherein the neutral oxalate salt is dipotassium oxalate.

3. A method as claimed in claim 1 wherein said effective amount of said neutral oxalate solution ranges from 1% w/v to saturation of said solution.

4. A method as claimed in claim 3 wherein the amount of said neutral solution is 30% w/v.

5. A method as claimed in claim 1 wherein said acidic oxalate salt is monopotassium monohydrogen oxalate.

6. A method as claimed in claim 1 wherein said effective amount of said acidic oxalate solution ranges from 0.5% to 3% w/v.

7. A method as claimed in claim 1 wherein said neutral oxalate salt is selected from the group consisting of alkalai metal oxalates and ammonium oxalates.

8. A method as claimed in claim 1 wherein the pH of said acidic oxalate salt solution is 1.

9. A method as claimed in claim 1 wherein said predetermined amount of time ranges from 1 to 2 minutes.

* * * * *